(12) United States Patent
Lin et al.

(10) Patent No.: US 11,771,727 B2
(45) Date of Patent: Oct. 3, 2023

(54) TRADITIONAL CHINESE MEDICINE COMPOSITION AND PRODUCT FOR IMPROVING SLEEP BY BALANCING YIN AND YANG, METHOD FOR MAKING THE SAME AND USE THEREOF

(71) Applicant: Qingdao Baishishankang Traditional Chinese Medicine Technology Co., Ltd., Qingdao (CN)

(72) Inventors: Ping Lin, Qingdao (CN); Zixuan Lin, Qingdao (CN)

(73) Assignee: Qingdao Baishishankang Trad. Chinese Med. Co., Ltd, Pingdu (CN)

( * ) Notice: Subject to any disclaimer, the term of this patent is extended or adjusted under 35 U.S.C. 154(b) by 0 days.

(21) Appl. No.: 17/656,554

(22) Filed: Mar. 25, 2022

(65) Prior Publication Data
US 2023/0233636 A1    Jul. 27, 2023

(30) Foreign Application Priority Data

Jan. 13, 2022    (CN) .......................... 202210029358.1

(51) Int. Cl.
| | | |
|---|---|---|
| *A61K 36/232* | (2006.01) | |
| *A61K 36/605* | (2006.01) | |
| *A61K 36/77* | (2006.01) | |
| *A61K 36/076* | (2006.01) | |
| *A61K 36/8945* | (2006.01) | |
| *A61K 36/8969* | (2006.01) | |
| *A61K 36/482* | (2006.01) | |
| *A61K 36/23* | (2006.01) | |
| *A61K 36/725* | (2006.01) | |
| *A61K 36/9068* | (2006.01) | |
| *A61K 36/54* | (2006.01) | |
| *A61K 36/752* | (2006.01) | |
| *A61K 36/254* | (2006.01) | |
| *A61P 25/20* | (2006.01) | |
| *A61K 36/185* | (2006.01) | |
| *A61K 36/07* | (2006.01) | |

(52) U.S. Cl.
CPC ............ *A61K 36/232* (2013.01); *A61K 36/07* (2013.01); *A61K 36/076* (2013.01); *A61K 36/185* (2013.01); *A61K 36/23* (2013.01); *A61K 36/254* (2013.01); *A61K 36/482* (2013.01); *A61K 36/54* (2013.01); *A61K 36/605* (2013.01); *A61K 36/725* (2013.01); *A61K 36/752* (2013.01); *A61K 36/77* (2013.01); *A61K 36/8945* (2013.01); *A61K 36/8969* (2013.01); *A61K 36/9068* (2013.01); *A61P 25/20* (2018.01); *A61K 2236/15* (2013.01)

(58) Field of Classification Search
None
See application file for complete search history.

(56) References Cited

FOREIGN PATENT DOCUMENTS

| CN | 101991094 A | * | 3/2011 |
|---|---|---|---|
| CN | 105878795 A | * | 8/2016 |
| CN | 108653571 A | * | 10/2018 |
| CN | 109486628 A | * | 3/2019 |

OTHER PUBLICATIONS

Machine translation of CN 101991094A.*
Machine translation of CN 109486628A.*
Machine translation of CN 108653571A.*
Machine translation of CN 105878795A.*

* cited by examiner

*Primary Examiner* — H. Sarah Park
(74) *Attorney, Agent, or Firm* — Welsh Flaxman & Gitler LLC

(57) ABSTRACT

The disclosure relates to a traditional Chinese medicine composition and product for improving sleep by balancing yin and yang, a method for making the same and use thereof, and belongs to the technical field of traditional Chinese medicine. The disclosure provides a traditional Chinese medicine composition for improving sleep by balancing yin and yang, which has reasonable compatibility of all herbal medicines, nourishes yin to suppress yang, tonifies blood and promotes blood, regulates qi and soothes the nerves, and has the functions of reconciling yin and yang and balancing qi and blood. The composition may fundamentally improve sleep quality, with an effective rate of 100%. At the same time, all the medicines in the prescription are raw materials of medicine food homology, which are safe and effective, not cause side effects and mental dependence on the human body, and may be taken for a long time.

12 Claims, No Drawings

TRADITIONAL CHINESE MEDICINE COMPOSITION AND PRODUCT FOR IMPROVING SLEEP BY BALANCING YIN AND YANG, METHOD FOR MAKING THE SAME AND USE THEREOF

CROSS REFERENCE TO RELATED APPLICATION

This patent application claims the benefit and priority of Chinese Patent Application No. 202210029358.1, entitled 'Traditional Chinese Medicine Composition and Product for Improving Sleep by Balancing Yin and Yang, Method for Making the Same and Use Thereof' filed on Jan. 13, 2022, the disclosure of which is incorporated by reference herein in its entirety as part of the present application.

TECHNICAL FIELD

The disclosure relates to the technical field of traditional Chinese medicine, in particular to a traditional Chinese medicine composition and product for improving sleep by balancing yin and yang, a method for making the same and use thereof.

BACKGROUND ART

Insomnia is a sleep disorder, manifested as difficulty in falling asleep, an intermittent and broken sleep, an early wakeup with a subsequent sleep loosing, and feeling of lack of sleep, general weakness, and fatigue. Insomnia is mainly caused by environmental factors, psychological and spiritual factors. Psychological factors such as anxiety, irritability or depression, and unpleasant mood are all important causes for insomnia. The impact of life, the pressure of work and study, the scuppered plans, and changes in the social environment, etc., will result in people's psychological and physiological reactions, including abnormal function of nervous system, which leads to brain dysfunction, and finally insomnia occurs.

Traditional Chinese medicine believes that normal sleep is a result of natural and regular transformation of yin and yang. "Sleep derives from yin, and is dominated by mental activity. One will get good sleep when the mental activity calms, otherwise insomnia takes place" ; "blood and qi are the vitality of people", and when they serve the heart, the heart vitality is nourished; when they enter the liver, the liver gets soft; they are transformed into essence and get stored in kidneys; the mental activity calms when cardionephric harmony occurs. The etiology of insomnia is complicated, and the symptoms can be seen, but clinically, it is mostly caused by pathogen invasion, or lack of nourishment qi resulting from thinking, fatigue, physical weakness caused by long period of illness, imbalance of seven emotions, etc., especially excessive joy, anger, thinking or sadness. The disease is located in the heart, often involving kidneys, liver, spleen and gallbladder, and the pathogenesis is that the excess yang leads to yin deficiency and imbalance of yin and yang.

At present, the clinical treatment of insomnia is often dominated by western medicines, such as diazepam and other phenobarbiturates. These medicines are effective, but long-term use will cause certain side effects to the body, resulting in medicine resistance and dependence. Although related treatment measures exist in traditional Chinese medicine science, most of them focus on nourishing blood and calming the nerves. There are problems such as ineffective treatment, not for long-term use, and easy recurrence after medicine withdrawal.

SUMMARY

The purpose of the present disclosure is to provide a traditional Chinese medicine composition for improving sleep by balancing yin and yang, in which the herbal medicines in the prescription are synergistically used for compatibility to exert the effects of nourishing yin to suppress hyperactive yang, nourishing the blood and promoting blood circulation, and regulating qi and calming the nerves. It may balance yin and yang, effectively promote sleep and improve sleep quality.

In order to solve the above technical problems, the present disclosure provides the following technical solutions.

The disclosure provides a traditional Chinese medicine composition for improving sleep by balancing yin and yang, including the following raw materials by weight:

0.2-6 parts of *Radix angelica sinensis*, 0.1-6 parts of *Sesamum indicum*, 0.1-9 parts of *Mori fructus*, 0.2-6 parts of *Fructus lycii*, 0.2-8 parts of *Poria*, 0.1-6 parts of *Rhizoma dioscoreae*, 0.2-8 parts of *Rhizoma polygonati*, 0.1-5 parts of *Semen cassiae*, 0.2-5 parts of *Apium graveolens*, 0.2-9 parts of *Semen ziziphi spinosae*, 0.1-6 parts of *Hericium erinaceus*, 0.1-7 parts of *Rhizoma zingiberis*, 0.1-6 parts of *Cortex cinnamoni*, 0.1-6 parts of *Pericarpium citri reticulatae*, and 0.1-5 parts of *Acanthopanacis senticosi*.

In some embodiments, the traditional Chinese medicine composition includes the following raw materials by weight:

1.5-5 parts of *Radix angelica sinensis*, 1-5 parts of *Sesamum indicum*, 2.5-6 parts of *Mori fructus*, 1.2-5 parts of *Fructus lycii*, 1-6 parts of *Poria*, 2-5 parts of *Rhizoma dioscoreae*, 1.5-5 parts of *Rhizoma polygonati*, 1-3 parts of *Semen cassiae*, 1.5-3 parts of *Apium graveolens*, 1.0-6 parts of *Semen ziziphi spinosae*, 0.8-5 parts of *Hericium erinaceus*, 0.4-5 parts of *Rhizoma zingiberis*, 0.3-3 parts of *Cortex cinnamoni*, 0.5-4 parts of *Pericarpium citri reticulatae*, and 1-3 parts of *Acanthopanacis senticosi*.

In some embodiments the Chinese medicine composition includes the following raw materials by weight:

3 parts of *Radix angelica sinensis*, 3 parts of *Sesamum indicum*, 3 parts of *Mori fructus*, 2.5 parts of *Fructus lycii*, 4 parts of *Poria*, 3 parts of *Rhizoma dioscoreae*, 4 parts of *Rhizoma polygonati*, 2.5 parts of *Semen cassiae*, 2 parts of *Apium graveolens*, 4.5 parts of *Semen ziziphi spinosae*, 3.5 parts of *Hericium erinaceus*, 2.5 parts of *Rhizoma zingiberis* 2.5 parts of *Cortex cinnamoni*, and 1.5 parts of *Pericarpium citri reticulatae*, and 2 parts of *Acanthopanacis senticosi*.

In some embodiments, the *Acanthopanacis senticosi* is leaves and seeds of *Acanthopanacis senticosi*.

The disclosure provides a method for preparing the traditional Chinese medicine composition, and the method includes the following steps:

mixing *Radix angelica sinensis*, *Sesamum indicum*, *Mori fructus*, *Fructus lycii*, *Poria*, *Rhizoma dioscoreae*, *Rhizoma polygonati*, *Semen cassiae*, *Apium graveolens*, *Semen ziziphi spinosae*, *Hericium erinaceus*, *Rhizoma zingiberis*, *Cortex cinnamoni*, *Pericarpium citri reticulatae*, and *Acanthopanacis senticosi* in proportion by weight, drying and pulverizing to obtain the traditional Chinese medicine composition.

In some embodiments, the pulverizing generates a particle size less than or equal to 180 μm.

The present disclosure also provides a use of the traditional Chinese medicine composition in the preparation of health food, functional food or medicine for improving sleep.

The disclosure provides a traditional Chinese medicine composition for improving sleep by balancing yin and yang. The herbal medicines in the prescription are reasonably compatible and have a synergistic effect. In the prescription, *Semen ziziphi spinosae*, which nourishes heart and calms the nerves, *Hericium erinaceus*, which promotes digestion and treats vacuity, and *Acanthopanacis senticosi*, which invigorates qi and calms the nerves, are the principal medicine and work together to calm the nerves and improve sleep; *Sesamum indicum*, which invigorates liver and kidney to benefit essence and blood, *Mori fructus*, which nourishes blood and yin, *Fructus lycii*, which protects liver and nourishes yin, *Rhizoma polygonati*, which invigorates qi and nourishes yin, *Semen cassiae*, which clears asthenic heat, and *Apium graveolens*, which calms liver and clears heat, are minister medicine for nourishing yin to suppress yang; *Cortex cinnamoni*, which supplements fire and yang and guides fire to origin, *Pericarpium citri reticulatae*, which regulates qi and promotes appetite, *Radix angelica sinensis*, which promotes blood circulation and nourishes blood, *Poria*, which induces diuresis to alleviate edema, and *Rhizoma dioscoreae*, which nourishes yin and invigorates qi, are used as adjuvant medicine; *Rhizoma zingiberis*, which warms middle energizer to dispel cold, and balances the cold nature of medicines, acts as assist medicine. The compatibility of the whole prescription is reasonable, which nourishes yin to suppress yang, nourishes blood and promotes blood circulation, and regulates qi and soothe the nerves. At the same time, all the medicines in the prescription are raw materials with medicine food homology, which are safe and effective, will not cause side effects and mental dependence on the human body, and can be administered for a long time.

DETAILED DESCRIPTION OF THE EMBODIMENTS

The disclosure provides a traditional Chinese medicine composition for improving sleep, comprising the following raw materials by weight:

0.2-6 parts of *Radix angelica sinensis*, 0.1-6 parts of *Sesamum indicum*, 0.1-9 parts of *Mori fructus*, 0.2-6 parts of *Fructus lycii*, 0.2-8 parts of *Poria*, 0.1-6 parts of *Rhizoma dioscoreae*, 0.2-8 parts of *Rhizoma polygonati*, 0.1-5 parts of *Semen cassiae*, 0.2-5 parts of *Apium graveolens*, 0.2-9 parts of *Semen ziziphi spinosae*, 0.1-6 parts of *Hericium erinaceus*, 0.1-7 parts of *Rhizoma zingiberis*, 0.1-6 parts of *Cortex cinnamoni*, 0.1-6 parts of *Pericarpium citri reticulatae*, and 0.1-5 parts of *Acanthopanacis senticosi*.

In the present disclosure, the *Radix angelica sinensis* is preferably 1.5-5 parts by weight, more preferably 3 parts by weight. The *Radix angelica sinensis* is warm in nature, sweet and acrid in flavour, and enters the liver meridian, heart meridian and spleen meridian. It nourishes blood and promotes blood circulation, regulates menstruation and relieve pain, relaxes bowel, and belongs to a blood nourishing medicine under the subclass of tonic medicine. Clinically, it is commonly used in the treatment of etiolate due to blood deficiency, dizziness and palpitations, irregular menstruation, amenorrhea and dysmenorrhea, abdominal pain due to asthenic cold, constipation, rheumatic arthralgia, injury from falls, and carbuncle sores.

In the present disclosure, the *Sesamum indicum* is preferably 1-5 parts by weight, more preferably 3 parts by weight. The *Sesamum indicum* is neutral in nature, sweet in flavour, and enters liver meridian, kidney meridian and large intestine meridian. It has the effects of invigorating liver and kidney, nourishing essence and blood, and relaxing bowel, and belongs to a blood nourishing medicine under the subclass of tonic medicine. It is commonly used in clinical treatment for dizziness, tinnitus, deafness, premature graying of beard and hair, hair loss after illness, constipation, liver and kidney deficiency, wind arthralgia, paralysis, and lack of breast milk in women; it can reduce blood glucose, increase the content of glycogen in liver and muscle, increase the anti-thrombotic and cholesterol content in the adrenal gland, prevent senility, excite the uterus, laxative, and inhibit the function of the adrenal cortex.

In the present disclosure, the *Mori fructus* is preferably 2.5-6 parts by weight, more preferably 3 parts by weight. The *Mori fructus* is cold in nature, sweet and sour in flavour, and enters the heart meridian, liver meridian and kidney meridian. It has the functions of replenishing blood and yin, promoting fluid production, and belongs to a blood nourishing medicine under the subclass of tonic medicine. It is commonly used in clinical treatment for dizziness, tinnitus, palpitations, insomnia, premature whitening of beard and hair, thirst due to body fluid deficiency, diabetes due to endohyrexia, and constipation due to blood deficiency. It has the effect of enhancing immune function and reducing the activity of $Na^+$-$K^+$-ATPase.

In the present disclosure, the *Fructus lycii* is preferably 1.2-5 parts by weight, more preferably 2.5 parts by weight. The *Fructus lycii* is neutral in nature, sweet in flavour, and enters the liver and kidney meridian. It has the effects of invigorating the liver and kidney, and improving eyesight, and belongs to a yin-tonifying medicine under the subclass of tonic medicine. Clinically, it is commonly used to treat consumptive disease due to deficiency, waist and knee pain, dizziness and tinnitus, diabetes due to intrinsic heat, etiolate due to blood deficiency, and blurred vision. It can enhance immune function, delay aging, anti tumor, lower blood lipids, protect liver, promote hematopoiesis, resist genetic damage, lower blood glucose and blood pressure, generate cholinergic effects such as heart inhibition and intestinal excitement, and enhance the hypoxia tolerance and increase the swimming time of mice.

In the present disclosure, the *Poria* is preferably 1-6 parts by weight, more preferably 4 parts by weight. The *Poria* is neutral in nature, sweet and light in flavour, and enters the heart meridian, lung meridian, spleen meridian, and kidney meridian. It has the effects of promoting diuresis and removing dampness, invigorating the spleen and calming the heart, and belongs to a medicine for inducing diuresis to alleviate edema under the subclass of medicines for promoting diuresis and removing dampness. It is commonly used to treat edema and oliguria, phlegmatic retention and dizziness, lack of appetite due to spleen deficiency, loose stools and diarrhea, restlessness, palpitation and insomnia.

In the present disclosure, the *Rhizoma dioscoreae* is preferably 2-5 parts by weight, more preferably 3 parts by weight. The *Rhizoma dioscoreae* is neutral in nature, sweet in flavour. It mainly treats acu-injury of diaphragm, invigorates deficiency, removes cold and heat pathogen, reinforces the middle warmer energy, boosts physical strength, grows muscles, and reinforces yin essence. As "Shennong's Herbal Classic Herbal" recorded, eating *Rhizoma dioscoreae* for a long time makes good sight and an exquisite sense of hearing, refreshes the body so that one are not prone to be hungry, and prolongs life. Quan Zhen pointed out that *Rhizoma dioscoreae* repairs five kinds of strain and seven kinds of impairments, removes cold pathogens, calms the mind, soothes the soul, replenishes heart qi, and improves intelligence and memory.

In the present disclosure, the *Rhizoma polygonati* is preferably 1.5-5 parts by weight, more preferably 4 parts by weight. The *Rhizoma polygonati* is neutral in nature, sweet in flavour, and enters the lung, spleen, and kidney meridians. It has the effects of tonifying qi and nourishing yin, strengthening the spleen, moistening the lungs, and benefiting the kidney, and belongs to a yin-tonifying medicine under the subclass of deficiency-reinforcing medicine.

In the present disclosure, the *Semen cassiae* is preferably 1-3 parts by weight, more preferably 2.5 parts by weight. The *Semen cassiae* is slightly cold in nature, bitter and sweet in flavour, and enters the liver meridian, kidney meridian, and large intestine meridian. It has the effects of clearing heat, improving eyesight, relaxing bowel, and belongs to a heat-clearing medicine under the subclass of heat-clearing medicines. Clinically, it is commonly used to treat swelling and pain of the eyes, photophobia and delacrimation, and night blindness caused by lift and attack of deficient fire or wind-heat in the liver meridian; constipation due to heat and intestinal dryness; dizziness and headache due to hyperactivity of liver yang, etc.

In the present disclosure, the *Apium graveolens* is preferably 1.5-3 parts by weight, more preferably 2 parts by weight. The *Apium graveolens* is cool in nature, sweet and acrid in flavour, and enters the liver, gallbladder, and pericardium meridians. It has the effects of clearing heat and dampness, calming the liver and invigorating the stomach. Clinically, it is used to treat hypertension, headache, dizziness, high fever and excessive thirst, jaundice, edema, difficult urination, irregular menstruation in women, multicoloured leukorrhagia, scrofula, mumps and other symptoms. It is enriched in colloidal calcium carbonate, which is easily absorbed by the human body.

In the present disclosure, the *Semen ziziphi spinosae* is preferably 1.0-6 parts by weight, more preferably 4.5 parts by weight. The *Semen ziziphi spinosae* is neutral in nature, sweet and sour in flavour, and enters the heart, liver and gallbladder meridians. As recorded in "Mingyi Bielu", *Semen ziziphi spinosae* mainly treats insomnia caused by vexation, consumptive sweating, and polydipsia, reinforces the middle warmer energy, benefits liver qi, strengthens muscles and bones, and fosters yin qi. "Compendium of Materia Medica" described that *Semen ziziphi spinosae* is sweet and moist, so it is cooked for therapeutic use in insomnia caused by gallbladder deficiency, and polydipsia with cold sweat. It has the effects of nourishing the heart and benefiting the liver, soothing the nerves, and arresting sweating.

In the present disclosure, the *Hericium erinaceus* is preferably 0.8-5 parts by weight, more preferably 3.5 parts by weight. The *Hericium erinaceus* is a kind of fungus with both medicinal and edible values, which is neutral in nature and sweet in flavour. It is very useful for treatment of loose stools, gastric and duodenal ulcers, neurasthenia, esophageal cancer, gastric cancer, dizziness, impotence and other diseases.

In the present disclosure, the *Rhizoma zingiberis* is preferably 0.4-5 parts by weight, more preferably 2.5 parts by weight. The *Rhizoma zingiberis* is hot in nature, acrid in flavour, and enters the spleen meridian, stomach meridian, heart meridian, kidney meridian, and lung meridian. It has the effects of warming middle energizer and expelling cold, recuperating depleted yang and invigorating pulse beat, and drying dampness and dispelling phlegm. It is commonly used in clinical treatment of stomach duct and abdomen aches due to cold, cold limbs and weak pulse, phlegmatic retention and cough with asthma, stagnant abdominal pain and gastrointestinal colic, rheumatism, low back and leg pain, gastric and duodenal ulcers, acute bacillary dysentery, acute orchitis, Ascariasis, intestinal obstruction, and chronic indigestion.

In the present disclosure, the *Cortex cinnamoni* is preferably 0.3-3 parts by weight, more preferably 2.5 parts by weight. The *Cortex cinnamoni* is hot in nature, acrid and sweet in flavour, and enters the kidney, spleen, heart, and liver meridians. It has the functions of supplementing fire and yang, guiding fire to the origin, dispelling cold and relieving pain, and warming the meridians and freeing vessels, and belongs to a interior-warming medicine.

In the present disclosure, the *Pericarpium citri reticulatae* is preferably 0.5-4 parts by weight, more preferably 1.5 parts by weight. The *Pericarpium citri reticulatae* is acrid and bitter in flavour, warm in nature, and enters the spleen meridian and lung meridian. It has the functions of regulating qi and promoting appetite, drying dampness and resolving phlegm, and curing spleen and stomach diseases, and belongs to a qi regulating medicine. Clinically, it is commonly used for the treatment of chest distress and abdominal distention, inappetence and vomiting, and cough and expectoration.

In the present disclosure, *Acanthopanacis senticosi* is preferably 1-3 parts by weight, more preferably 2 parts by weight. The *Acanthopanacis senticosi* is preferably from *Acanthopanax senticosus* (Rupr. et Maxim.) Harms, the *Acanthopanacis senticosi* is warm in nature, acrid and slightly bitter in flavour, and enters spleen meridian, kidney meridian, and heart meridian. It has the effects of replenishing qi to invigorate the spleen, tonifying kidney and calming the nerves, and belongs to a qi replenishing medicine under the subclass of deficiency-reinforcing medicine. Clinically, it is commonly used to treat yang deficiency of spleen and kidney, soreness and weakness of waist and knees, fatigue and hypodynamia, insomnia, dreaminess and loss of appetite.

The disclosure provides a preparation method of the traditional Chinese medicine composition, and the method includes the following steps:

mixing *Radix angelica sinensis*, *Sesamum indicum*, *Mori fructus*, *Fructus lycii*, *Poria*, Chinese *Rhizoma dioscoreae*, *Rhizoma polygonati*, *Semen cassiae*, *Apium graveolens*, *Semen ziziphi spinosae*, *Hericium erinaceus*, *Rhizoma zingiberis*, *Cortex cinnamoni*, *Pericarpium citri reticulatae*, and *Acanthopanacis senticosi* in proportion by weight, drying and pulverizing to obtain a traditional Chinese medicine composition.

In the present disclosure, the pulverizing preferably generates a particle size of ≤180 μm, more preferably ≤150 μm. Method of the drying and pulverizing is not particularly limited in the present disclosure, and a conventional drying and pulverizing method in the art can be adopted.

The present disclosure also provides a product for improving sleep, including the traditional Chinese medicine composition. In the present disclosure, the products preferably include health food and medicines; the health food preferably includes candy bars and drinks, and the medicines preferably include powders, tablets, granules, capsules, solutions, emulsions, suspensions or pills. The present disclosure does not pose limitations on the preparation method of the product, and on the basis of ensuring the active ingredients of the traditional Chinese medicine composition, the preparation can be carried out according to a conventional preparation method in the art.

The present disclosure also provides a use of the traditional Chinese medicine composition in the preparation of health food or medicine for improving sleep. The present disclosure does not specifically pose limitations on the method of administration, and a conventional administering method for health food, functional food or medicine in the art can be used. In the present disclosure, administration of the composition preferably includes directly drinking the composition powder mixed with hot water, or swallowing the traditional Chinese medicine composition that is pressed into tablets, or chewing the traditional Chinese medicine composition that is pressed into blocks or pills, or drinking the traditional Chinese medicine composition that is made into plant drinks.

In the present disclosure, the raw materials, reagents and equipment used are all known products, and conventional commercially available products can be used.

In the present disclosure, the methods, unless otherwise specified, are conventional methods in the art.

In order to further illustrate the present disclosure, the technical solutions provided by the present disclosure are described in detail below with reference to the examples, but they should not be construed as limiting the protection scope of the present disclosure.

Example 1

0.2 part of *Radix angelica sinensis*, 0.1 part of *Sesamum indicum*, 0.1 part of *Mori fructus*, 0.2 part of *Fructus lycii*, 0.2 part of *Poria*, 0.1 part of *Rhizoma dioscoreae*, 0.2 part of *Rhizoma polygonati*, 0.1 part of *Semen cassiae*, 0.2 part of *Apium graveolens*, 0.2 part of *Semen ziziphi spinosae*, 0.1 part of *Hericium erinaceus*, 0.1 part of *Rhizoma zingiberis*, 0.1 part of *Cortex cinnamoni*, 0.1 part of *Pericarpium citri reticulatae*, and 0.1 part of *Acanthopanacis senticosi* were mixed, dried and pulverized into 180 μm fine powder to obtain the traditional Chinese medicine composition of the present disclosure.

Example 2

6 parts of *Radix angelica sinensis*, 6 parts of *Sesamum indicum*, 9 parts of *Mori fructus*, 6 parts of *Fructus lycii*, 8 parts of tuckahoe, 6 parts of *Rhizoma dioscoreae*, 8 parts of *Rhizoma polygonati*, 5 parts of *Semen cassiae*, 5 parts of *Apium graveolens*, 9 parts of *Semen ziziphi spinosae*, 6 parts of *Hericium erinaceus*, 7 parts of *Rhizoma zingiberis*, 6 parts of *Cortex cinnamoni*, 6 parts of *Pericarpium citri reticulatae*, and 5 parts of *Acanthopanacis senticosi* were mixed, dried and pulverized into 170 μm fine powder to obtain the traditional Chinese medicine composition of the present disclosure.

Example 3

3 parts of *Radix angelica sinensis*, 3 parts of *Sesamum indicum*, 3 parts of *Mori fructus*, 2.5 parts of *Fructus lycii*, 4 parts of *Poria*, 3 parts of *Rhizoma dioscoreae*, 4 parts of *Rhizoma polygonati*, 2.5 parts of *Semen cassiae*, 2 parts of *Apium graveolens*, 4.5 parts of *Semen ziziphi spinosae*, 3.5 parts of *Hericium erinaceus*, 2.5 parts of *Rhizoma zingiberis*, 2.5 parts of *Cortex cinnamoni*, 1.5 parts of *Pericarpium citri reticulatae*, and 2 parts of *Acanthopanacis senticosi* were mixed, dried and pulverized into 150 μm fine powder to obtain the traditional Chinese medicine composition of the present disclosure.

Example 4

Experimental study on effect of the composition on improving sleep

1. Animals and groups 1.1 Healthy SPF-grade mice with the same development status and a weight of 20±2 g were taken for the experiment.

1.2 80 mice were randomly divided into 4 groups, with 20 mice in each group, which were respectively blank control group, low-dose treatment group, medium-dose treatment group and high-dose treatment group; in which, the blank control group was treated with 0.01 mL/g purified water by oral administration according to the weight of the mice. The treatment group was treated with the traditional Chinese medicine composition prepared in Example 3 of the present disclosure by oral administration. Specifically, the active ingredient content of the low-dose treatment group was 0.6 g/kg/d, which was equivalent to 0.5 times the usual dose of the prescription for human; The active ingredient content of the medium-dose group was 1.2 g/kg/d, which was equivalent to the usual dose of the prescription for human, and the active ingredient content of the high-dose treatment group was 12 g/kg/d, which was equivalent to 10 times the usual dose of the prescription for human. Mice in each group were given continuous gavage for 15 days, and allowed to freely drink water and eat food at other times.

Sleep was indexed by disappearance of righting reflex in mice. When the mice were placed in the supine position, those who could not straighten their bodies to the prone position within 30 s were considered to have no righting reflex and entered sleep. The recovery of the righting reflex was regarded as awakening, and the time between the disappearance of the righting reflex and the recovery was the sleep time of the animal.

2. Sleep time by pentobarbital sodium was prolonged 15 min after the last gavage, the animals in each group were intraperitoneally injected with sodium pentobarbital at 45 mg/kg, the injection volume was 0.1 mL/10 g, and the sleeping time of sodium pentobarbital was recorded. The results are shown in Table 1.

TABLE 1

Results of prolonging the sleep time of pentobarbital sodium in mice

| Group | Blank Group control | Treatment group | | |
|---|---|---|---|---|
| | | Low-dose | Medium-dose | High-dose |
| Sleep time (min) | 11.0 ± 4.35 | 15.35 ± 1.98 | 20.26 ± 4.0 | 25.38 ± 3.35 |

3. Hypnosis experiment at subthreshold dose of pentobarbital sodium 15 min after the last gavage, the animals in each group were intraperitoneally injected with pentobarbital sodium at 45 mg/kg, the injection volume was 0.1 ml/10 g, and the sleep time by pentobarbital sodium was recorded. The results are shown in Table 2.

TABLE 2

Influence on the hypnotic effect of pentobarbital sodium subthreshold dose

| Group | Blank Group control | Treatment group | | |
|---|---|---|---|---|
| | | Low-dose | Medium-dose | High-dose |
| Number of mice falling asleep | 3 | 8 | 12 | 18 |
| Sleep incidence (%) | 15 | 40 | 60 | 90 |

4. Sleep latency test by pentobarbital sodium 15 minutes after the last gavage, animals in each group were intraperitoneally injected with pentobarbital sodium at 45 mg/kg, the injection volume was 0.1 ml/10 g, and the sleep latency of the mice was recorded. The results are shown in Table 3.

TABLE 3

Sleep latency test by barbital sodium

| Group | Blank Group control | Treatment group | | |
| --- | --- | --- | --- | --- |
| | | Low-dose | Medium-dose | High-dose |
| Sleep latency (min) | 13.5 ± 1.8 | 10.3 ± 1.5 | 9.0 ± 1.3 | 8.2 ± 1.2 |

Overall evaluation: of the sleep latency test by pentobarbital sodium, sleep time test by pentobarbital sodium, sleep incidence test by pentobarbital sodium, if 2 of the 3 experiments are positive, it can be determined that the test sample has the effect of improving sleep.

It could be seen that the traditional Chinese medicine composition provided by the present disclosure significantly shortened the sleep latency time by sodium pentobarbital, prolonged the sleep time induced by sodium pentobarbital, and improve the incidence of hypnosis at subthreshold dose of pentobarbital sodium. All experiments were positive, so the traditional Chinese medicine composition of the present disclosure has the effect of improving sleep obviously.

Example 5

Clinical use 100 patients with sleep disorders, both male and female, were randomly selected. All patients had difficulty falling asleep and waking up easily. After waking up, it was difficult to fall asleep, or even unable to continue to sleep. At the same time, they were accompanied by symptoms of insomnia such as headache, dizziness, irritability, forgetfulness and dreaminess.

The traditional Chinese medicine composition described in Examples 1-3 of the present disclosure was taken with hot water, 3 times a day, 2-4 g each time, and the curative effect was observed after taking it for half a month. The results are shown in Table 4.

TABLE 4

Observation of curative effect

| Group | Cases | Cure | Improvement | Ineffective | Effective Rate |
| --- | --- | --- | --- | --- | --- |
| Example 1 | 35 | 30 | 4 | 1 | 97.1% |
| Example 2 | 32 | 29 | 3 | 0 | 100% |
| Example 3 | 33 | 30 | 3 | 0 | 100% |

In which, "cure" means the sleep disorder is eliminated, falling asleep within five minutes of lying down, sleeping soundly all night, and the sleep time being at least 8 hours;

"improvement" means sleep disorders are greatly improved, falling asleep within five minutes of lying down, occasionally waking up at night, and the overall sleep time reaching 6-8 hours;

"ineffective" means there are still symptoms of insomnia, having difficulty in falling asleep, being easy to wake up, and having difficulty in falling asleep after waking up.

It could be seen from the above examples that the traditional Chinese medicine composition for improving sleep by balancing yin and yang provided in the present disclosure, which is reasonable in compatibility, nourishes yin to suppress yang, tonifies blood and promotes blood circulation, regulates qi and soothes the nerves, and has the functions of reconciling yin and yang and balancing qi and blood, was confirmed by experiments to be capable of fundamentally improving sleep quality, with an effective rate of 100%. At the same time, all the medicines in the prescription are raw materials with medicinal food homology, which are safe and effective, not cause side effects and mental dependence on the human body, and may be taken for a long time.

The above descriptions are only some embodiments of the present disclosure, and are not intended to limit the scope of the patent of the present disclosure. Any equivalent structure or equivalent process transformation made by adopting the contents of the description of the present disclosure, or directly or indirectly applied in other related technical fields, are all included in the protection scope of the present disclosure.

What is claimed is:

1. A traditional Chinese medicine composition for improving sleep comprising the following raw materials by weight:
    2-6 parts of *Radix angelica sinensis*, 0.1-6 parts of *Sesamum indicum*, 0.1-9 parts of *Mori fructus*, 0.2-6 parts of *Fructus lycii*, 0.2-8 parts of *Poria*, 0.1-6 parts of *Rhizoma dioscoreae*, 0.2-8 parts of *Rhizoma polygonati*, 0.1-5 parts of *Semen cassiae*, 0.2-5 parts of *Apium graveolens*, 0.2-9 parts of *Semen ziziphi spinosae*, 0.1-6 parts of *Hericium erinaceus*, 0.1-7 parts of *Rhizoma zingiberis*, 0.1-6 parts of *Cortex cinnamoni*, 0.1-6 parts of *Pericarpium citri reticulatae*, and 0.1-5 parts of *Acanthopanacis senticosi*.

2. The traditional Chinese medicine composition of claim 1, wherein the composition comprises the following raw materials by weight:
    1.5-5 parts of *Radix angelica sinensis*, 1-5 parts of *Sesamum indicum*, 2.5-6 parts of *Mori fructus*, 1.2-5 parts of *Fructus lycii*, 1-6 parts of *Poria*, 2-5 parts of *Rhizoma dioscoreae*, 1.5-5 parts of *Rhizoma polygonati*, 1-3 parts of *Semen cassiae*, 1.5-3 parts of *Apium graveolens*, 1.0-6 parts of *Semen ziziphi spinosae*, 0.8-5 parts of *Hericium erinaceus*, 0.4-5 parts of *Rhizoma zingiberis*, 0.3-3 parts of *Cortex cinnamoni*, 0.5-4 parts of *Pericarpium citri reticulatae*, and 1-3 parts of *Acanthopanacis senticosi*.

3. The traditional Chinese medicine composition of claim 1, wherein the composition comprises the following raw materials by weight:
    3 parts of *Radix angelica sinensis*, 3 parts of *Sesamum indicum*, 3 parts of *Mori fructus*, 2.5 parts of *Fructus lycii*, 4 parts of *Poria*, 3 parts of *Rhizoma dioscoreae*, 4 parts of *Rhizoma polygonati*, 2.5 parts of *Semen cassiae*, 2 parts of *Apium graveolens*, 4.5 parts of *Semen ziziphi spinosae*, 3.5 parts of *Hericium erinaceus*, 2.5 parts of *Rhizoma zingiberis* 2.5 parts of *Cortex cinnamoni*, and 1.5 parts of *Pericarpium citri reticulatae*, and 2 parts of *Acanthopanacis senticosi*.

4. The traditional Chinese medicine composition of claim 1, wherein the *Acanthopanacis senticosi* is leaves and seeds of *Acanthopanacis senticosi*.

5. A method for preparing the Chinese medicine composition of any one of claims 1-3, the method comprising the following steps:
    mixing the raw materials in proportion by weight, drying and pulverizing to obtain a traditional Chinese medicine composition.

6. The method of claim 5, wherein the pulverizing generates a particle size of ≤180 μm.

7. A method for improving sleep, comprising administering a health food, a functional food or an effective therapeutic dose of medicine comprising the traditional Chinese medicine composition of claim 1 to a patient in need thereof.

8. The composition of claim 4, wherein the composition comprises the following raw materials by weight:

1.5-5 parts of *Radix angelica sinensis*, 1-5 parts of *Sesamum indicum*, 2.5-6 parts of *Mori fructus*, 1.2-5 parts of *Fructus lycii*, 1-6 parts of *Poria*, 2-5 parts of *Rhizoma dioscoreae*, 1.5-5 parts of *Rhizoma polygonati*, 1-3 parts of *Semen cassiae*, 1.5-3 parts of *Apium graveolens*, 1.0-6 parts of *Semen ziziphi spinosae*, 0.8-5 parts of *Hericium erinaceus*, 0.4-5 parts of *Rhizoma zingiberis*, 0.3-3 parts of *Cortex cinnamoni*, 0.5-4 parts of *Pericarpium citri reticulatae*, and 1-3 parts of *Acanthopanacis senticosi*.

9. The composition of claim 4, wherein the composition comprises the following raw materials by weight:

3 parts of *Radix angelica sinensis*, 3 parts of *Sesamum indicum*, 3 parts of *Mori fructus*, 2.5 parts of *Fructus lycii*, 4 parts of *Poria*, 3 parts of *Rhizoma dioscoreae*, 4 parts of *Rhizoma polygonati*, 2.5 parts of *Semen cassiae*, 2 parts of *Apium graveolens*, 4.5 parts of *Semen ziziphi spinosae*, 3.5 parts of *Hericium erinaceus*, 2.5 parts of *Rhizoma zingiberis* 2.5 parts of *Cortex cinnamoni*, and 1.5 parts of *Pericarpium citri reticulatae*, and 2 parts of *Acanthopanacis senticosi*.

10. The method of claim 7, wherein the composition comprises the following raw materials by weight:

1.5-5 parts of *Radix angelica sinensis*, 1-5 parts of *Sesamum indicum*, 2.5-6 parts of *Mori fructus*, 1.2-5 parts of *Fructus lycii*, 1-6 parts of *Poria*, 2-5 parts of *Rhizoma dioscoreae*, 1.5-5 parts of *Rhizoma polygonati*, 1-3 parts of *Semen cassiae*, 1.5-3 parts of *Apium graveolens*, 1.0-6 parts of *Semen ziziphi spinosae*, 0.8-5 parts of *Hericium erinaceus*, 0.4-5 parts of *Rhizoma zingiberis*, 0.3-3 parts of *Cortex cinnamoni*, 0.5-4 parts of *Pericarpium citri reticulatae*, and 1-3 parts of *Acanthopanacis senticosi*.

11. The method of claim 7, wherein the composition comprises the following raw materials by weight:

3 parts of *Radix angelica sinensis*, 3 parts of *Sesamum indicum*, 3 parts of *Mori fructus*, 2.5 parts of *Fructus lycii*, 4 parts of *Poria*, 3 parts of *Rhizoma dioscoreae*, 4 parts of *Rhizoma polygonati*, 2.5 parts of *Semen cassiae*, 2 parts of *Apium graveolens*, 4.5 parts of *Semen ziziphi spinosae*, 3.5 parts of *Hericium erinaceus*, 2.5 parts of *Rhizoma zingiberis*, 2.5 parts of *Cortex cinnamoni*, 1.5 parts of *Pericarpium citri reticulatae*, and 2 parts of *Acanthopanacis senticosi*.

12. The method of claim 7, wherein the effective therapeutic dose is 5-15 g/kg/d.

* * * * *